(12) United States Patent
Sinambela et al.

(10) Patent No.: US 9,131,723 B2
(45) Date of Patent: Sep. 15, 2015

(54) SUBSTANTIALLY COUMARIN-FREE EXTRACT OF CINNAMON AND ITS PRODUCTION METHOD

(75) Inventors: James M. Sinambela, Bekasi (ID); Veronika Yuliani, Jakarta Selatan (ID); Deasy Diah Dwi Retno Wulan, Cimahi (ID); Raymond R. Tjandrawinata, Jakarta Selatan (ID)

(73) Assignee: PT. DEXA MEDICA, Sumatera Selatan (ID)

( * ) Notice: Subject to any disclaimer, the term of this patent is extended or adjusted under 35 U.S.C. 154(b) by 0 days.

(21) Appl. No.: 13/882,502

(22) PCT Filed: Nov. 23, 2010

(86) PCT No.: PCT/IB2010/055366
§ 371 (c)(1),
(2), (4) Date: Jun. 21, 2013

(87) PCT Pub. No.: WO2012/069876
PCT Pub. Date: May 31, 2012

(65) Prior Publication Data
US 2013/0344181 A1  Dec. 26, 2013

(51) Int. Cl.
*A61K 36/54* (2006.01)
*A23L 1/30* (2006.01)

(52) U.S. Cl.
CPC ............... *A23L 1/3002* (2013.01); *A61K 36/54* (2013.01); *A61K 2236/33* (2013.01); *A61K 2236/39* (2013.01)

(58) Field of Classification Search
CPC .. A61K 36/54; A61K 36/353; A61K 2236/30
See application file for complete search history.

(56) References Cited

FOREIGN PATENT DOCUMENTS

FR  2933301 A1  1/2010
JP  58129002 A * 8/1983

OTHER PUBLICATIONS

Mohammed et al. (2011) Kufa Journal for Veterinary Medical Science vol. (2) No. (2) pp. 91-101.*
Oct. 2008, Subehan, Shigetoshi Kadota, Yasuhiro Tezuka: "In vitro mechanism-based inactivation of cytochrome P450 3A4 by a new constituent of Cinnamomum burmani", Planta Medica, vol. 74, No. 12, Oct. 2008, pp. 1474-1480, XP009145605, ISSN: 0032-0943, D01: D01:10.1055/S-2008-1081351 p. 1475.
Sep. 16, 2009, Database WPI Week 200967 Thomson Scientific. London, GB; AN 2009-P00862 XP002626652, & CN 101 530 469 A (Sun Y) Sep. 16, 2009 abstract.
Jun. 13, 2007, Shan Bin et al: "Antibacterial properties and major bioactive components of cinnamon stick (Cinnamomum burmannii): Activity against foodborne pathogenic bacteria", Journal of Agricultural and Food Chemistry. American Chemical Society, US, vol. 55. No. 14. Jul. 1, 2007, pp. 5484-5490. XP002514013, ISSN: 0021-8561, DOI: DOI:10.1021/JF070424D [retrieved on Jun. 13, 2007] p. 5485, left-hand column.
Jan. 5, 2008, Chua et al: "Antioxidant activities of ethanolic extracts from the twigs of Cinnamomum osmophloeum", Bioresource Technology. Elsevier BV, GB, vol. 99, No. 6, Jan. 5, 2008, pp. 1918-1925, XP022410823, ISSN: 0960-8524, DOI:DOI:10.1016/J.Biortech. 2007.03.020 p. 1919. left-hand column.
Jan. 1, 1988, Archer A W: "Determination of Cinnamaldehyde, Coumarin and Cinnamyl Alcohol in Cinnamon and Cassia by High-Performance Liquid Chromatography", Elsevier Science Publishers B.V, NL, vol. 447. No. 1. Jan. 1, 1988, pp. 272-276. XP009016010, ISSN: 0021-9673 p. 275; table 1.
Sep. 2010, Germany, Bundesamt Fuer Verbraucherschutz Und Lebensmittelsicherheit: "Analysis of foods. Determination of coumarin in cinnamon-containing foods by HPLC/DAD or HPLC-MS/MS", International Food Information Service (IFIS), Frankfurt-AM-Main, No. L00.00-134, Sep. 2010, p. 6PP., XP9145602, Amtliche Sammlung Von Unterschungsverfahren Nach Paragraph 64 LFGB Paragraph 35 Vorlaeufiges Tabakgesetz Paragraph 28B Gentg 2010 the whole document.
PCT Search Report for PCT/IB2010/055366.
PCT Written Opinion for PCT/IB2010/055366.

* cited by examiner

*Primary Examiner* — Chris R Tate
*Assistant Examiner* — Russell Fiebig
(74) *Attorney, Agent, or Firm* — Neifeld IP Law, PC (57) ABSTRACT

A pharmaceutical composition comprising a substantially coumarin-free extract derived from cinnamon. Its production method including some steps: grinding the raw material, extracting raw material from previous step by maceration using a first solvent to obtain crude extract of *Cinnamomum burmanii*, fractionating the extracted raw material from previous step through liquid-liquid extraction using a second solvent, wherein the second solvent is immiscible with the first solvent to obtain substantially coumarin-free extract, and optionally drying the substantially coumarin-free extract.
The pharmaceutical composition comprising the substantially coumarin-free extract as a single component or in a combination with suitable pharmaceutical excipient(s) to produce a pharmaceutical composition that is safe to be consumed daily and in long-term use.

2 Claims, 14 Drawing Sheets

SUBSTANTIALLY COUMARIN-FREE EXTRACT OF CINNAMON AND ITS PRODUCTION METHOD

CROSS REFERENCE TO RELATED APPLICATIONS

This application is a national stage entry of PCT/IB2010/055366, filed Nov. 23, 2010, which published as WO 2012/069876 on May 31, 2012.

FIELD OF THE INVENTION

The present invention relates to a process for the production of a substantially coumarin-free extract of *Cinnamomum burmanii*. The present invention also relates to a pharmaceutical composition and dietary supplement comprising the substantially coumarin-free extract of *Cinnamomum burmanii*.

BACKGROUND OF THE INVENTION

*Cinnamomum burmanii* is one of Indonesian native plants which has been known empirically for its potency as medicament. *Cinnamomum burmanii* is commonly referred to as cinnamon. Cinnamon-based products have been marketed for some time now as food supplement and indicated to treat various diseases. However, despite its therapeutic effect, it has been known recently that most of cinnamon products extracted from cinnamon plants contain high level of coumarin.

Coumarin is a natural benzopyron compound present in several plants including cinnamon, tonka beans, vanili and *Cuscuta reflexa* (a medicinal herb). It has been widely known and used since 1882 as one of the components in production of perfume. For medicinal usage, coumarin is a precursor in production of anticoagulant. However, coumarin can become toxic to liver especially after long-term use.

European Safety Authority (ESA) recommends a Tolerable Daily Intake (TDI) of coumarin as 0.1 mg coumarin per kilogram body weight which can be ingested daily over a lifetime without posing a risk to health.

To date, there is no *Cinnamomum burmanii* extract currently available in the market which has low level of coumarin. People usually use alternative source of cinnamon including *Cinnamomum zeylanicum* since its coumarin level is low and considered as safe. However, *Cinnamomum zeylanicum* is more expensive, thus it is not economical for large industrial application. Consequently, there is a need to develop an extract of *Cinnamomum burmanii* which has substantially coumarin-free. The present invention taught a production process of *Cinnamomum burmanii* extract which is substantially free of coumarin so it can be consumed safely for a long-term use.

BRIEF DESCRIPTION OF THE INVENTION

The objects and/or solutions which are taught from the present invention will be set forth in the preferred embodiments. The embodiments illustrated serve the purpose of understanding the present invention, without limiting the possibilities of other embodiments which can be learned from the practice of the present invention. The objects and/or solutions which are taught in the present invention will be realized from the elements and combinations detailed in the claims herein.

To attain the solutions and in accordance with the objects of the present invention, as explained in the embodiments and broadly described in this application, the first aspect of the present invention is directed to a process for the preparation of substantially coumarin-free extract of *Cinnamomum burmanii*, through an extraction process followed by a fractionation process based on the relative solubility in two different immiscible liquids. This process is currently known as liquid-liquid extraction.

The second aspect of the present invention is directed to a substantially coumarin-free extract of *Cinnamomum burmanii* as a single active ingredient or in combination, wherein the coumarin level in the said extract is equal or below 0.39 mg coumarin/kg extract.

The third aspect of the present invention is directed to a pharmaceutical composition or preparation which comprises the substantially coumarin-free extract of *Cinnamomum burmanii* as a single active ingredient or in combination, wherein the coumarin level in the said extract is equal or below 0.39 mg coumarin/kg extract.

BRIEF DESCRIPTION OF DRAWINGS

The following drawings, which are incorporated in and constitute a part of the specification of the present application, illustrate one or several embodiments of the invention. The following drawings serve to explain the principles which are taught by the present invention.

8 and 9 were crude extracts of *Cinnamomum burmanii* fractionated using ethyl acetate; and 10 and 11 were crude extracts of *Cinnamomum burmanii* fractionated using n-hexane.

1 was coumarin standard, 2 and 3 were crude extracts of *Cinnamomum burmanii* extracted using acetone, 4 and 5 were crude extracts of *Cinnamomum burmanii* fractionated using chloroform.

6 and 7 were crude extracts of *Cinnamomum burmanii* fractionated using n-butanol.

8 and 9 were crude extracts of *Cinnamomum burmanii* fractionated using ethyl acetate; and 10 and 11 were crude extracts of *Cinnamomum burmanii* fractionated using n-hexane.

DETAILED DESCRIPTION OF THE INVENTION

The present invention will be discussed in details by giving examples without limiting the scope of the invention to the examples described.

This invention is generally divided into two major steps including, first step, extraction of *Cinnamomum burmanii* using first solvent including but not limited to water and/or various organic solvents including but not limited to alcohols, acetone to produce a crude extract; second step, fractionation of the crude extract using other organic solvent(s) which is immiscible with the first solvent(s) including but not limited to chloroform, n-butanol, ethyl acetate or n-hexane to get an extract which is substantially free from coumarin. Analytical observations using Thin Layer Chromatography (TLC) and High Performance Liquid Chromatography (HPLC) were performed.

According to the teaching of the present invention, the term "substantially coumarin-free" means a condition whereby the level of coumarin is under the limit of Tolerable Daily Intake (TDI) proposed by European Safety Authority (ESA). Raw material is natural material that has not gone through any extraction process; crude extract is an extract that has not gone through the fractionation process; and substantially coumarin-free extract is an extract that has gone through an extraction process followed by fractionation process and whereby the level of coumarin is under the limit of Tolerable Daily Intake (TDI) proposed by European Safety Authority (ESA).

In accordance with the teaching of the invention, the extraction process can be done using various solvents, including water, alcohols, acetone, or combination thereof. The coumarin content, resulted from the extraction process using any solvents, varies depending on the quality of raw material as well as the solubility of coumarin in the solvents used.

The fractionation process performed subsequent to the extraction process is done repeatedly until the level of coumarin content has reached at certain target.

A. Extraction Process Using Water and Coumarin Removal Therefrom

A substantially coumarin-free *Cinnamomum burmanii* extract according to the teaching of the present invention is prepared using water-based extraction method. Coumarin is highly soluble in hot water hence a common water extraction causes a high content of coumarin in the *Cinnamomum burmanii* extract solution.

Extraction process using water was initialized by grinding any part of the *Cinnamomum burmanii* plants preferably the bark portion. It was then followed by maceration in hot water with temperature in the range of 50-100° C. in 5-15 times the volume of the raw material of ground *Cinnamomum burmanii* bark for 1-2 hour(s). Filtration process was performed to get the filtrate which was then concentrated by evaporating the filtrate to reach viscosity in the range of 40-100 cps. The viscosity of the concentrate was measured using Brookfields DV-E-Viscometer with spindle #61, at 27° C., 100 rpm for 2 minutes. Hence, a crude extract of *Cinnamomum burmanii* is obtained.

In order to reduce the content of coumarin in the crude extract, the concentrate was then fractionated based on the relative solubility by liquid-liquid extraction (LLE) using organic solvent(s) including but not limited to chloroform, n-butanol, ethyl acetate and/or n-hexane. The ratio of the crude extract compared to fractionation solvent is approximately 1:1 to 1:2. The mixture was gently shaken to avoid the formation of emulsion. The LLE was performed repeatedly until the crude extract of the *Cinnamomum burmanii* was substantially free from coumarin. The analysis on coumarin content was performed on Thin Layer Chromatography (TLC) and High Performance Liquid Chromatography (HPLC). TLC and HPLC analysis will be explained further detail below. Finally, the extract of the *Cinnamomum burmanii* substantially free from coumarin was dried.

B. Extraction Process Using Alcohols and Coumarin Removal Therefrom

Alternatively, a substantially coumarin-free *Cinnamomum burmanii* extract according to the teaching of the present invention can also be prepared through an extraction process using alcohol. Coumarin is easily soluble in alcohol causing the alcohol based *Cinnamomum burmanii* extract to contain a high level of coumarin.

Alcohols used according to the teaching of this invention include but not limited to methanol, ethanol, and butanol. Ethanol and methanol are preferred. Extraction process using alcohol was initialized by grinding any part of *Cinnamomum burmanii* preferably the bark portion followed by maceration in ethanol or methanol in 5-15 times the volume of the raw material for 1-2 hour(s). In this example the alcohol content in water was not more than 70%. Filtration process was performed to get a filtrate which was then concentrated by evaporating the filtrate to reach viscosity in the range of 40-100 cps. The viscosity of the concentrate was measured using Brookfields DV-E-Viscometer with spindle #61, at 27° C., 100 rpm for 2 minutes. Hence, a crude extract of *Cinnamomum burmanii* is obtained.

In order to eliminate the content of coumarin present in the crude extract, the concentrate was then fractionated by liquid-liquid extraction using organic solvent(s) including but not limited to chloroform, n-butanol, ethyl acetate and/or n-hexane. The ratio of the crude extract compared to fractionation solvent is approximately 1:1 to 1:2. The mixture was gently shaken to avoid the formation of emulsion. The LLE was performed repeatedly until the crude extract was substantially free from coumarin. The analysis on coumarin content was performed on Thin Layer Chromatography (TLC) and High Performance Liquid Chromatography (HPLC). After that, the extract of the *Cinnamomum burmanii* substantially free of coumarin was dried.

C. Extraction Process Using Acetone and Coumarin Removal Therefrom

Further alternatively, a substantially coumarin-free *Cinnamomum burmanii* extract according to the teaching of the present invention can also be prepared through an extraction process using acetone.

This extraction process was initialized by grinding any part of the *Cinnamomum burmanii* plant preferably the bark portion followed by maceration using acetone in 5-15 times the volume of the raw material for 1-2 hour(s). In this example the acetone content in water used was not more than 70%. Filtration process was performed to get the filtrate which was then concentrated by evaporating the filtrate to reach viscosity in the range of 40-100 cps. The viscosity of the concentrate was measured using Brookfields DV-E-Viscometer with spindle #61, at 27° C., 100 rpm for 2 minutes. Hence, a crude extract of *Cinnamomum burmanii* is obtained.

The concentrate was then fractionated by liquid-liquid extraction using organic solvent(s) including but not limited to chloroform, n-butanol, ethyl acetate and/or n-hexane. The ratio of crude extract compared to fractionation solvent is approximately 1:1 to 1:2. The mixture was shaken gently to avoid the formation of emulsion. LLE was performed repeatedly until the crude extract of *Cinnamomum burmanii* was substantially free from coumarin. The analysis was done on Thin Layer Chromatography (TLC) and High Performance Liquid Chromatography (HPLC). Similar to extraction process using water and alcohol, the extract of the Cinnamomum burmanii substantially free from coumarin was then dried.

D. Coumarin Content Analysis Using Thin Layer Chromatography (TLC)

This experiment was performed to ascertain the content of the extract of *Cinnamomum burmanii* was substantially free from coumarin. The extract of *Cinnamomum burmanii* obtained from several different extraction processes as discussed above were analyzed in Thin Layer Chromatography (TLC) plate. Crude extract and substantially coumarin-free extract of *Cinnamomum burmanii* in concentration of 4000 ppm were prepared and compared to coumarin standard in the same concentration. Elution was done using toluene and ethyl acetate (93:7) as mobile phase. The chromatogram was then observed under UV light at 254 nm and 366 nm, and under visible light as well.

Figure 1:
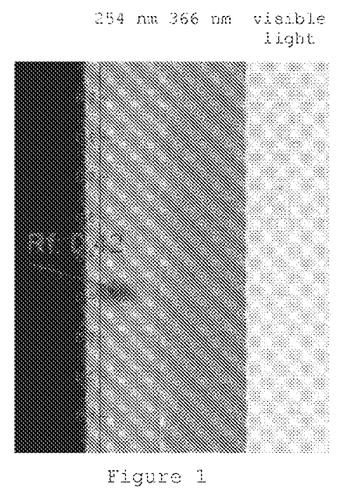
FIG. 1 is a thin layer chromatogram of coumarin standard.
Figure 2:
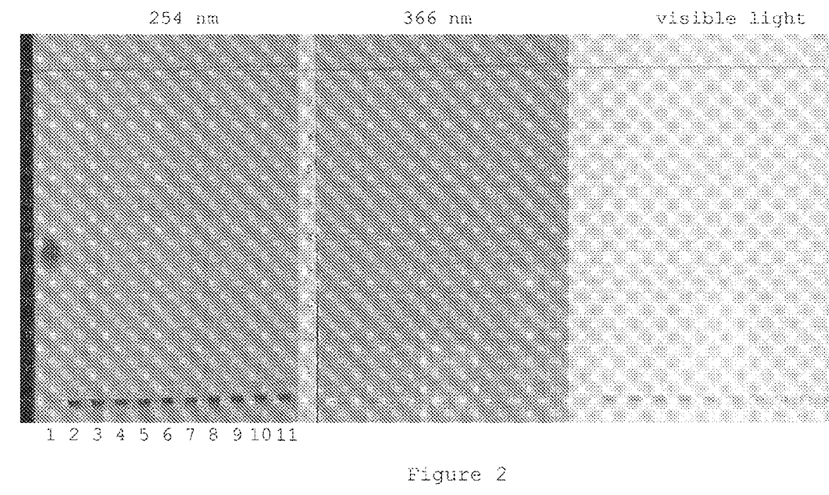
FIG. 2 is a thin layer chromatogram of crude extract of *Cinnamomum burmanii* extracted using water and its substantially coumarin-free extract prepared using chloroform, n-butanol, ethyl acetate, and n-hexane. Notes:
 1 was coumarin standard,
 2 and 3 were crude extracts of *Cinnamomum burmanii* extracted using water,
 4 and 5 were crude extracts of *Cinnamomum burmanii* fractionated using chloroform;
 6 and 7 were crude extracts of *Cinnamomum burmanii* fractionated using n-butanol;
 8 and 9 were crude extracts of *Cinnamomum burmanii* fractionated using ethyl acetate; and
 10 and 11 were crude extracts of *Cinnamomum burmanii* fractionated using n-hexane.
Figure 3:
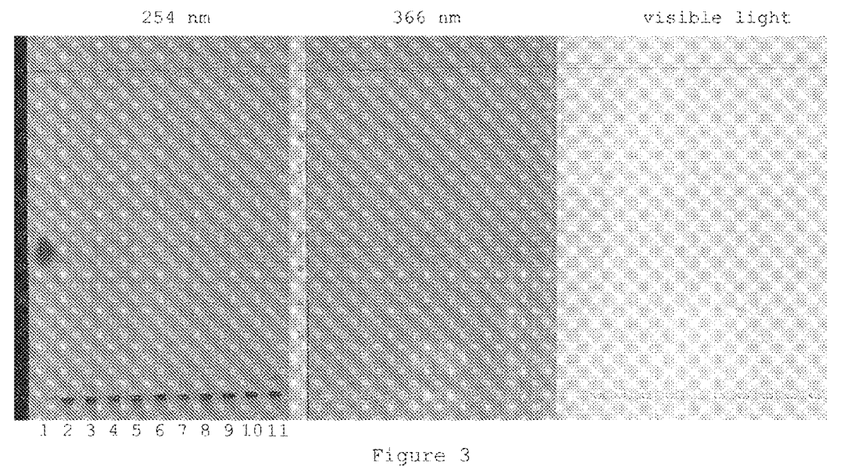
FIG. 3 is a thin layer chromatogram of crude extract of *Cinnamomum burmanii* extracted using methanol and its substantially coumarin-free extract prepared using chloroform, n-butanol, ethyl acetate, and n-hexane. Notes:
 1 was coumarin standard,
 2 and 3 were crude extracts of *Cinnamomum burmanii* extracted using methanol,
 4 and 5 were crude extracts of *Cinnamomum burmanii* fractionated using chloroform;
 6 and 7 were crude extracts of *Cinnamomum burmanii* fractionated using n-butanol;
 8 and 9 were crude extracts of *Cinnamomum burmanii* fractionated using ethyl acetate; and
 10 and 11 were crude extracts of *Cinnamomum burmanii* fractionated using n-hexane.
Figure 4:
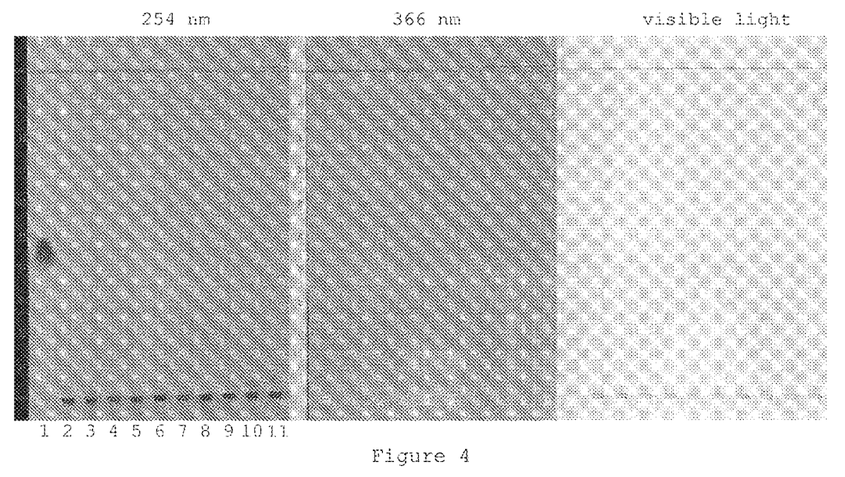
FIG. 4 is a thin layer chromatogram of crude extract of *Cinnamomum burmanii* extracted using ethanol and its polar extract prepared using chloroform, n-butanol, ethyl acetate, and n-hexane. Notes:
 1 was coumarin standard,
 2 and 3 were crude extracts of *Cinnamomum burmanii* extracted using ethanol,
 4 and 5 were crude extracts of *Cinnamomum burmanii* fractionated using chloroform;
 6 and 7 were crude extracts of *Cinnamomum burmanii* fractionated using n-butanol.
Figure 5:
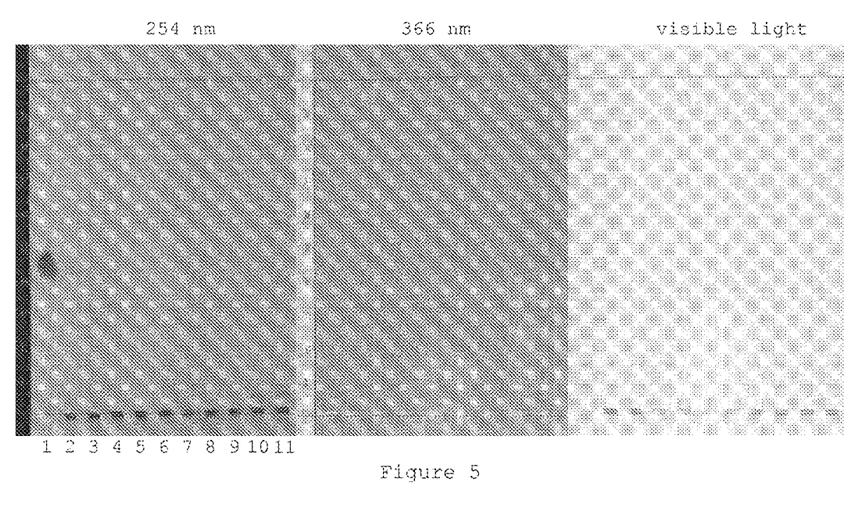
FIG. 5 is a thin layer chromatogram of crude extract of *Cinnamomum burmanii* extracted using acetone and its substantially coumarin-free extract prepared using chloroform, n-butanol, ethyl acetate, and n-hexane. Notes.
Figure 6:
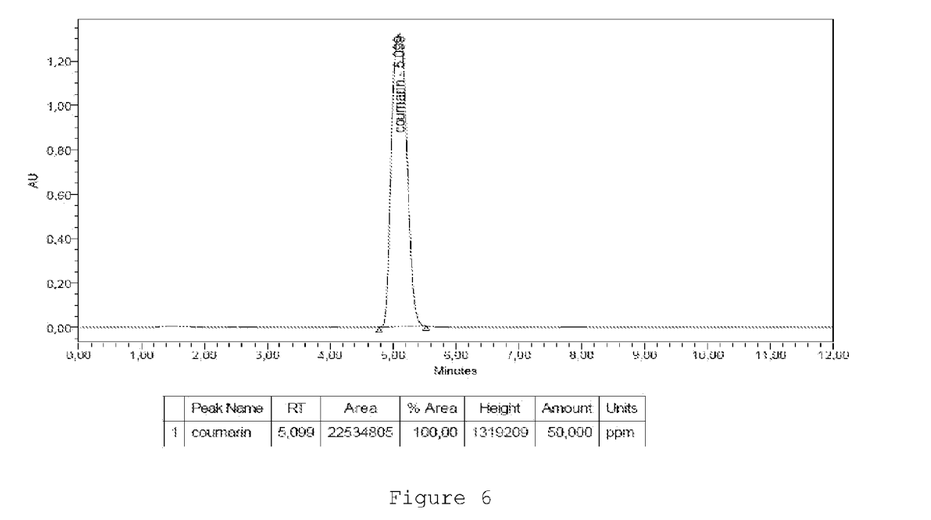
FIG. 6 is a high performance liquid chromatogram of standard coumarin compound.

Spot for standard coumarin compound was shown at Rf of 0.42. It was shown in lines 2 and 3 of each of FIGS. 4, 5, and 6 that only the crude extracts, prepared before fractionation through liquid-liquid extraction, had the same Rf with the standard coumarin compound. This can clearly be seen on the elution observed under UV light at 254 nm. On the other hand, as shown in lines 4-11 of each of FIGS. 4, 5, and 6, the substantially coumarin-free extract of *Cinnamomum burmanii*, which was the product of fractionation process using liquid-liquid extraction, did not show any spot around Rf 0.42 which represents the spot of coumarin compound. This indicated that the extract of *Cinnamomum burmanii* prepared according to the teaching of this present invention was substantially free from coumarin.

E. Coumarin Content Analysis Using High Performance Liquid Chromatography (HPLC)

Analysis using High Performance Liquid Chromatography (HPLC) Alliance 2695 with detector Photo Diode Array Alliance 2889 was performed to determine quantitatively the content of coumarin in the substantially coumarin-free extract of *Cinnamomum burmanii*.

The substantially coumarin-free extract of *Cinnamomum burmanii* was dried and then analyzed in HPLC. In this analysis, the crude extract and substantially coumarin-free extract of *Cinnamomum burmanii* were prepared in concentration of 4000 ppm and compared to coumarin standard in concentration of 50 ppm. Analysis process was done using mobile phase of water:acetonitril (60:40) which would be observed at 274 nm with retention time of 12 minutes.

Figure 7:
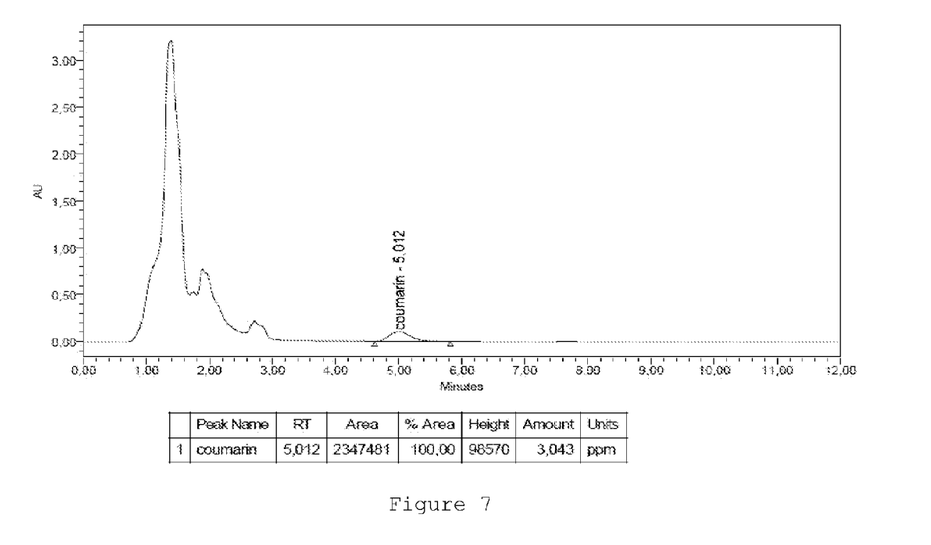
FIG. 7 is a high performance liquid chromatogram of crude extract of *Cinnamomum burmanii* extracted using water.
Figure 8:
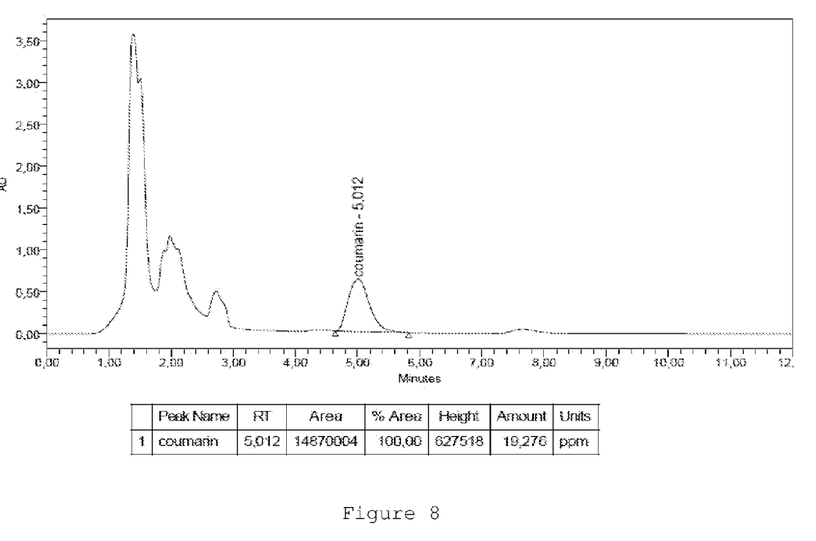
FIG. 8 is a high performance liquid chromatogram of crude extract of *Cinnamomum burmanii* extracted using methanol.
Figure 9:
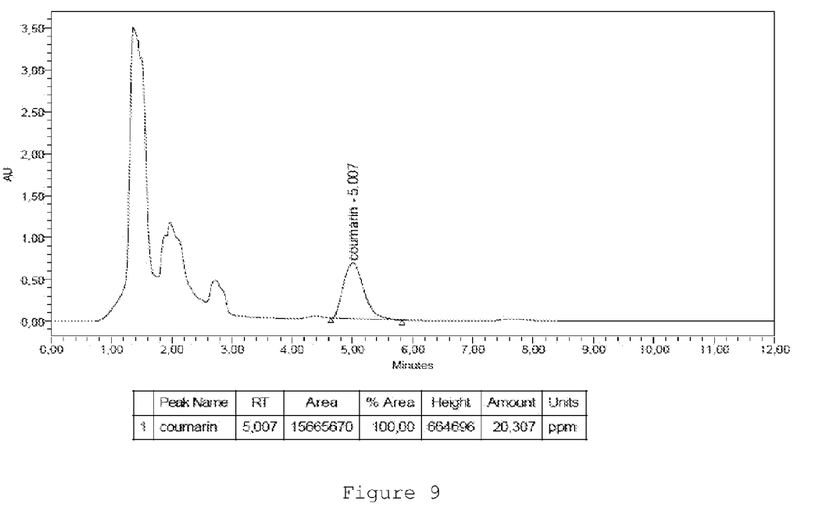
FIG. 9 is a high performance liquid chromatogram of crude extract of *Cinnamomum burmanii* extracted using ethanol.
Figure 10:
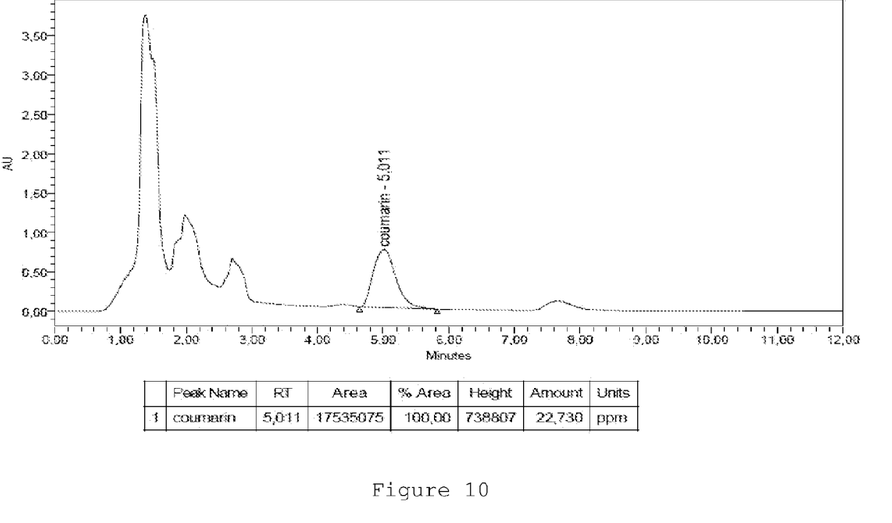
FIG. 10 is a high performance liquid chromatogram of crude extract of *Cinnamomum burmanii* extracted using acetone.
Figure 11:
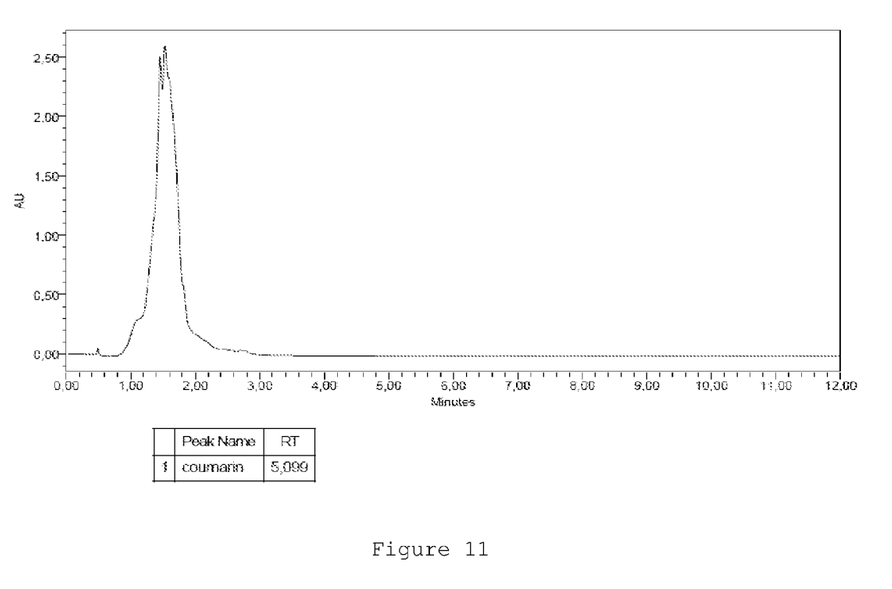
FIG. 11 is a high performance liquid chromatogram of substantially coumarin-free extract of *Cinnamomum burmanii* extracted using water and fractionated using chloroform.
Figure 12:
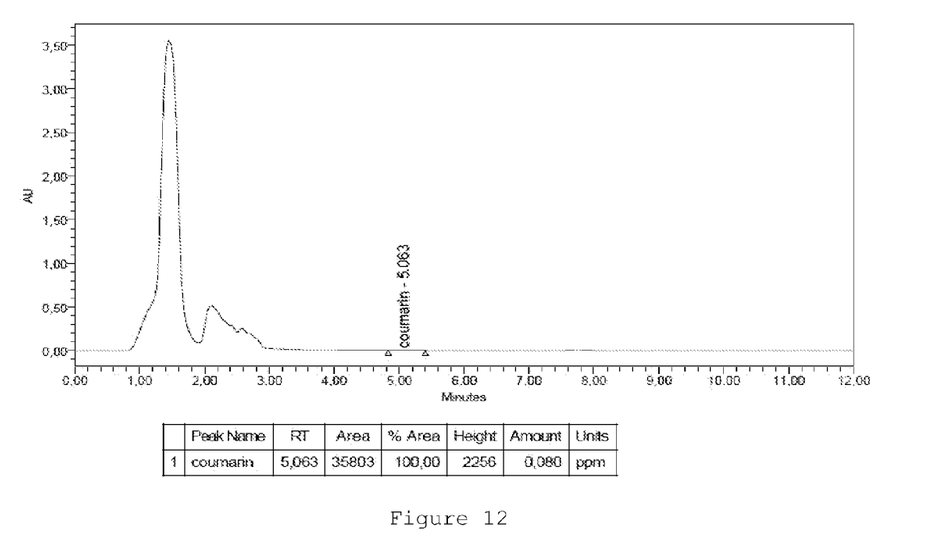
FIG. 12 is a high performance liquid chromatogram of substantially coumarin-free extract of *Cinnamomum burmanii* extracted using methanol and fractionated using chloroform.
Figure 13:
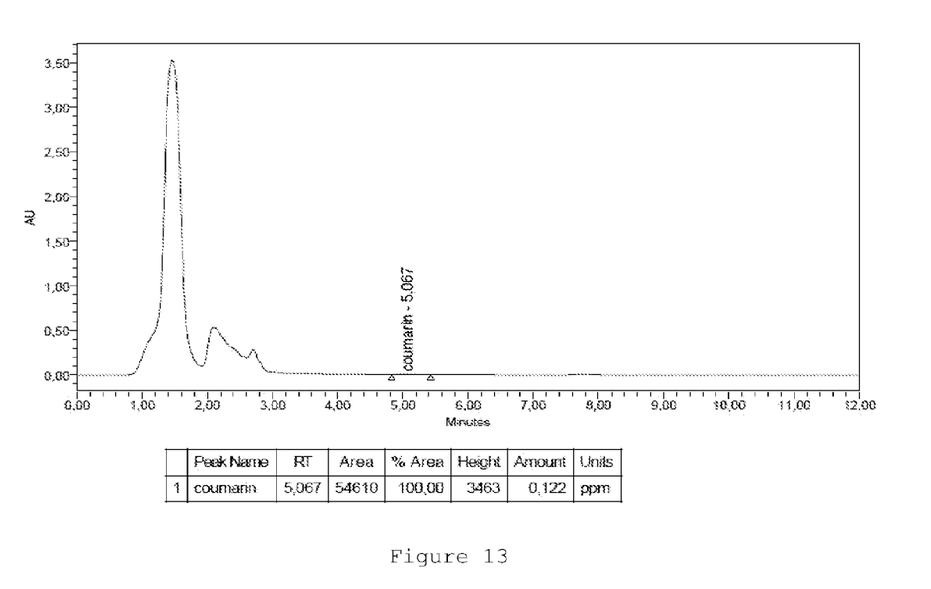
FIG. 13 is a high performance liquid chromatogram of substantially coumarin-free extract of *Cinnamomum burmanii* extracted using ethanol and fractionated using chloroform.
Figure 14:
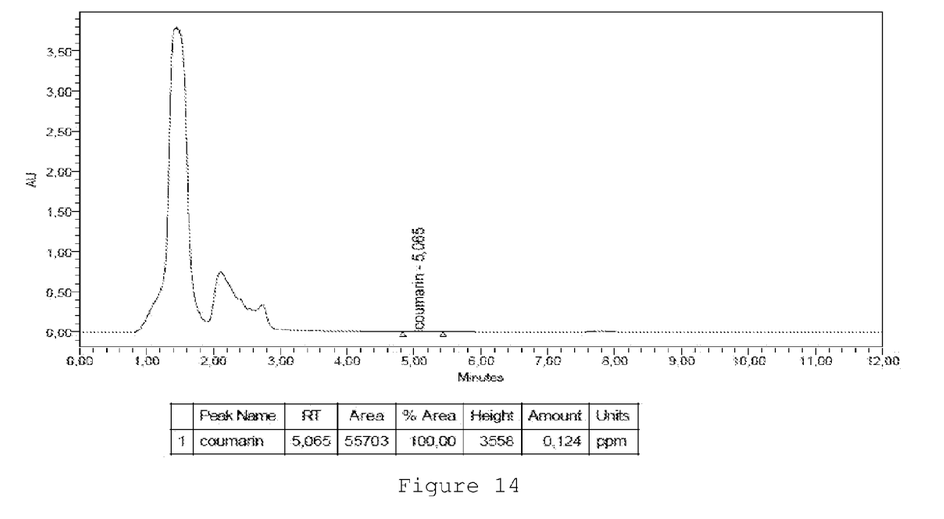
FIG. 14 is a high performance liquid chromatogram of substantially coumarin-free extract of *Cinnamomum burmanii* extracted using acetone and fractionated using chloroform.
Figure 15:
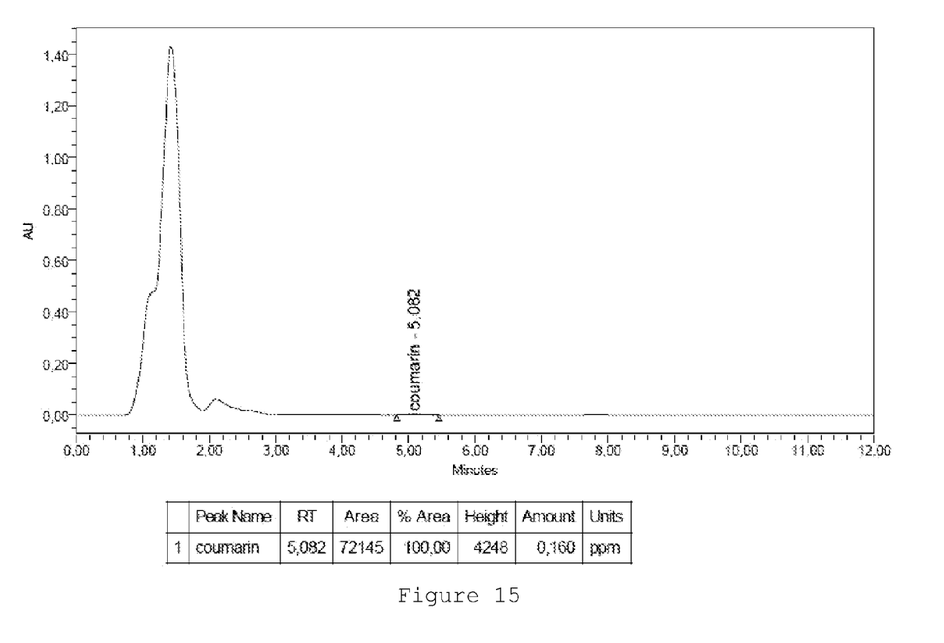
FIG. 15 is a high performance liquid chromatogram of substantially coumarin-free extract of *Cinnamomum burmanii* extracted using water and fractionated using n-butanol.
Figure 16:
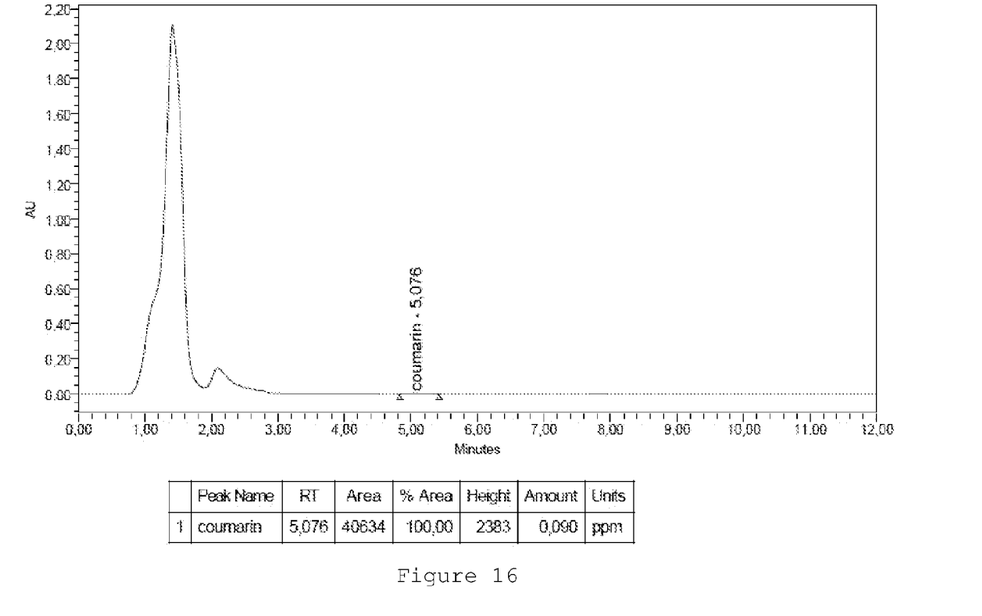
FIG. 16 is a high performance liquid chromatogram of substantially coumarin-free extract of *Cinnamomum burmanii* extracted using methanol and fractionated using n-butanol.
Figure 17:
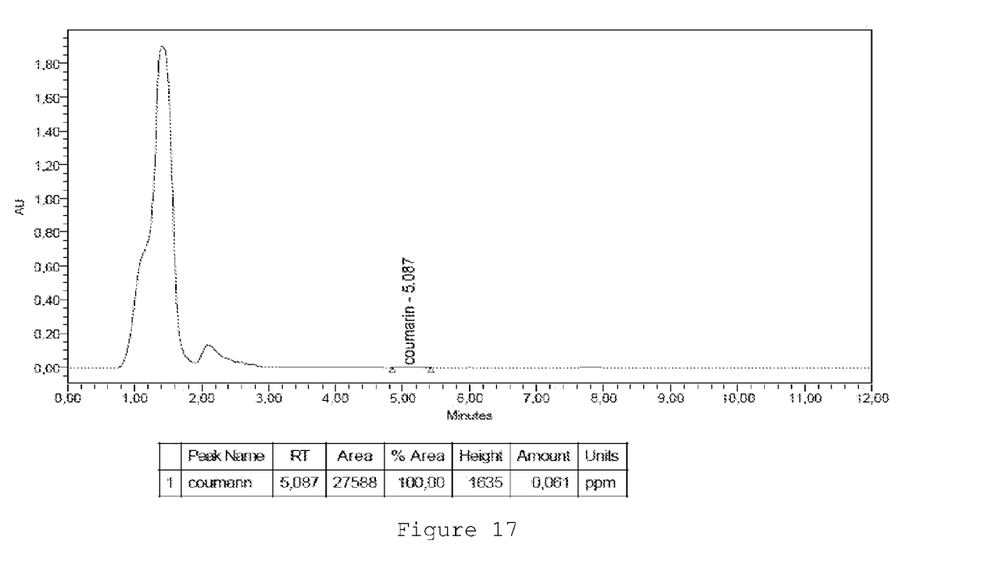
FIG. 17 is a high performance liquid chromatogram of substantially coumarin-free extract of *Cinnamomum burmanii* extracted using ethanol and fractionated using n-butanol.
Figure 18:
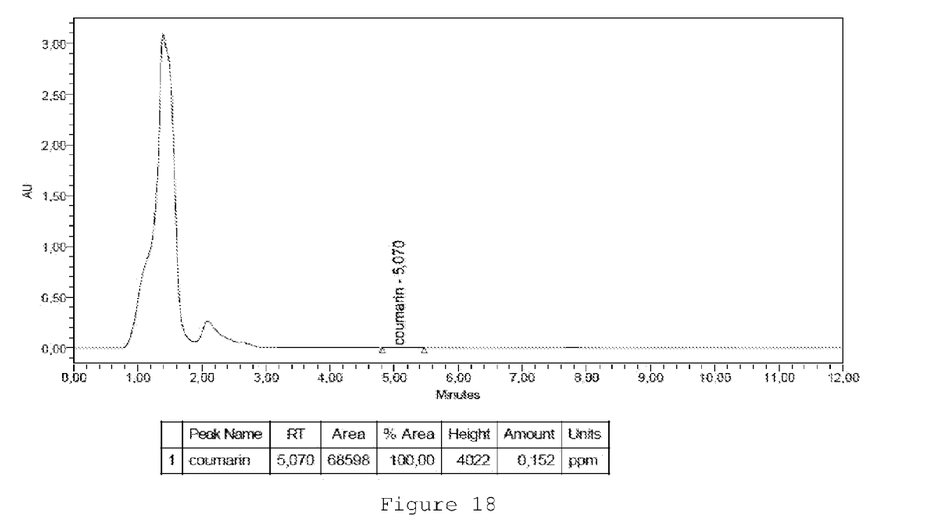
FIG. 18 is a high performance liquid chromatogram of substantially coumarin-free extract of *Cinnamomum burmanii* extracted using acetone and fractionated using n-butanol.
Figure 19:
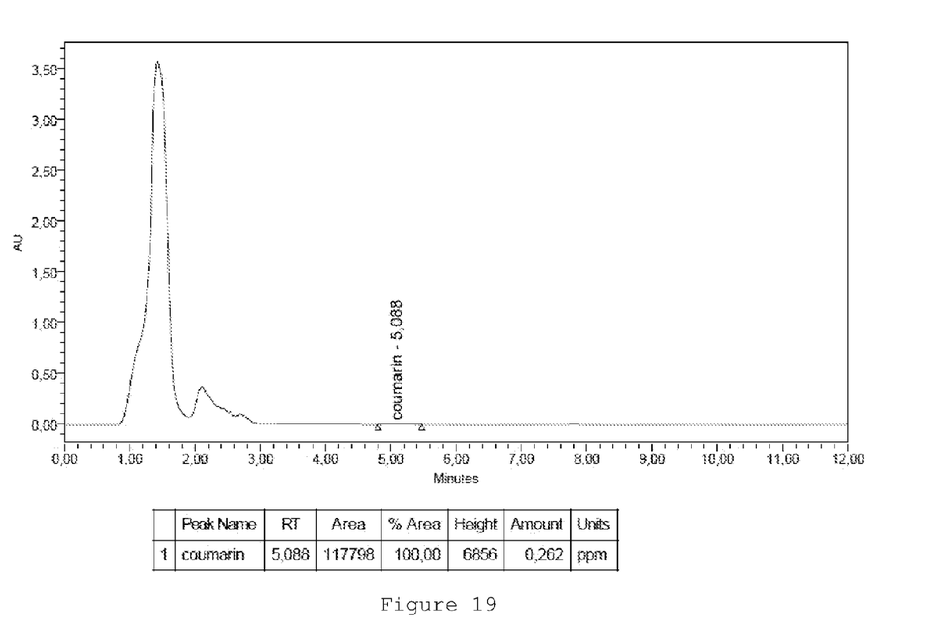
FIG. 19 is a high performance liquid chromatogram of substantially coumarin-free extract of *Cinnamomum burmanii* extracted using water and fractionated using ethyl acetate.
Figure 20:
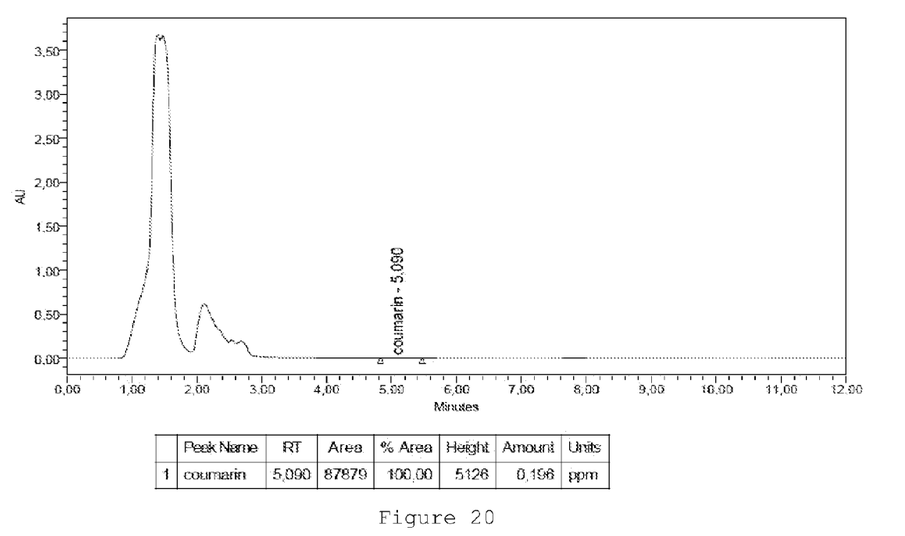
FIG. 20 is a high performance liquid chromatogram of substantially coumarin-free extract of *Cinnamomum burmanii* extracted using methanol and fractionated using ethyl acetate.
Figure 21:
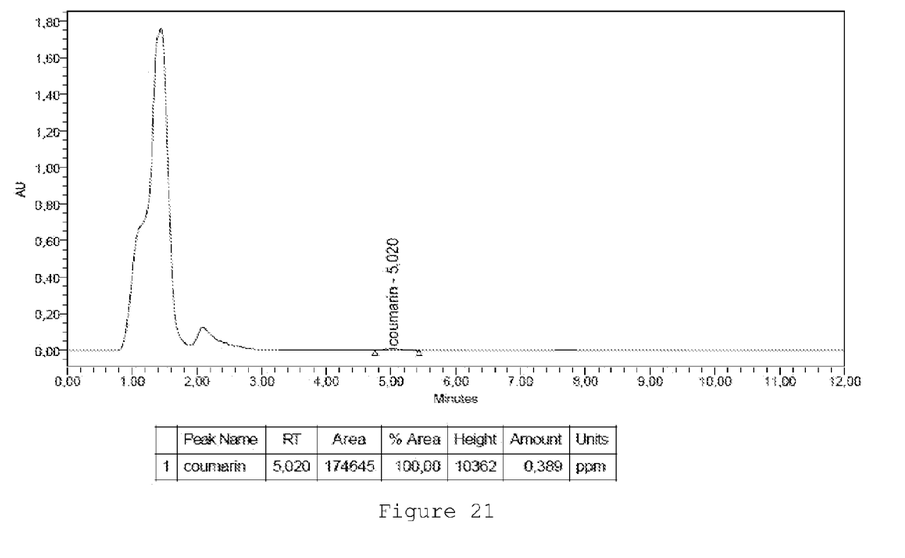
FIG. 21 is a high performance liquid chromatogram of substantially coumarin-free extract of *Cinnamomum burmanii* extracted using ethanol and fractionated using ethyl acetate.
Figure 22:
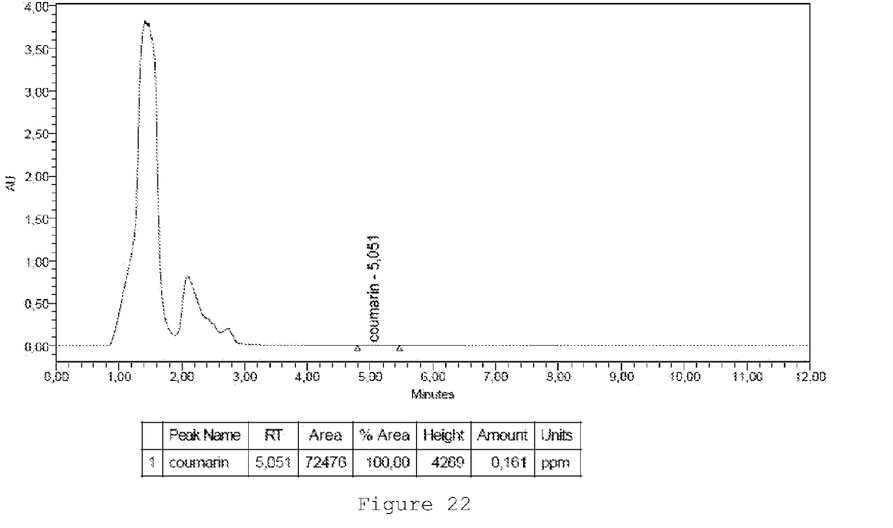
FIG. 22 is a high performance liquid chromatogram of substantially coumarin-free extract of *Cinnamomum burmanii* extracted using acetone and fractionated using ethyl acetate.
Figure 23:
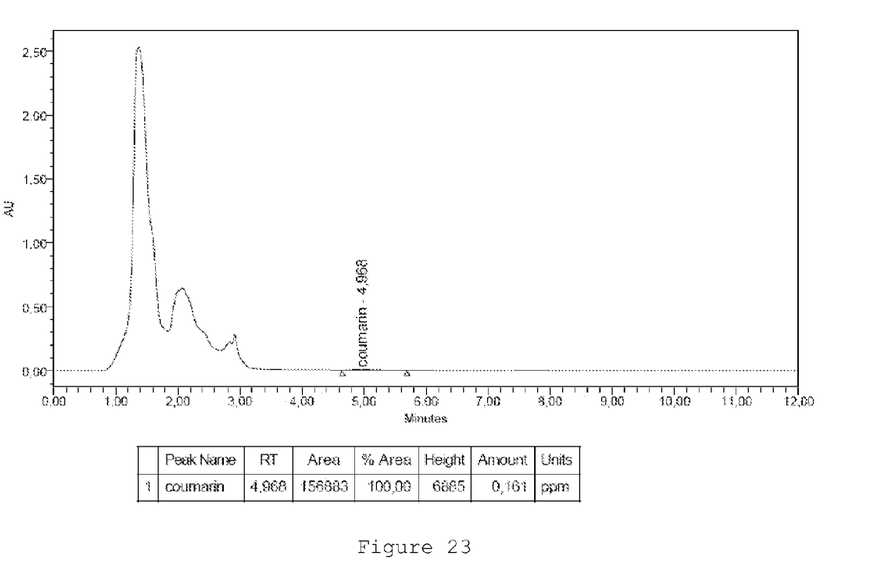
FIG. 23 is a high performance liquid chromatogram of substantially coumarin-free extract of *Cinnamomum burmanii* extracted using water and fractionated using n-hexane.
Figure 24:
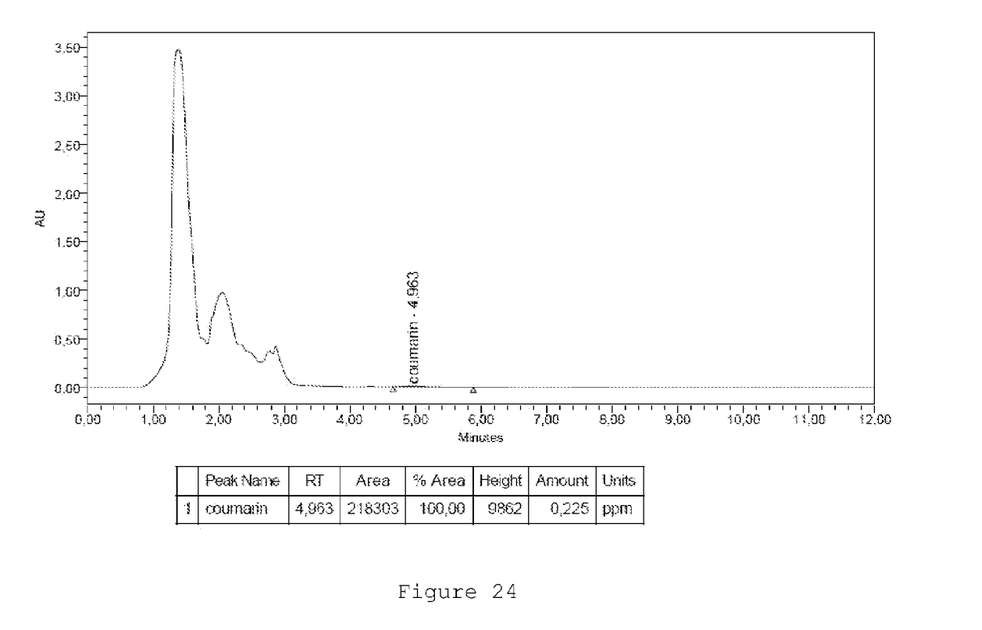
FIG. 24 is a high performance liquid chromatogram of substantially coumarin-free extract of *Cinnamomum burmanii* extracted using methanol and fractionated using n-hexane.
Figure 25:
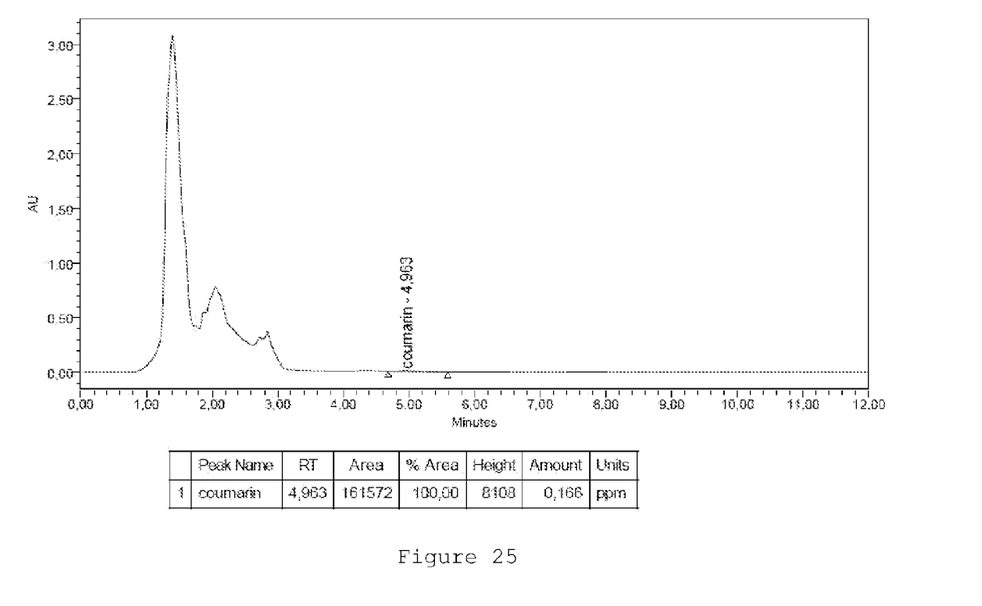
FIG. 25 is a high performance liquid chromatogram of substantially coumarin-free extract of *Cinnamomum burmanii* extracted using ethanol and fractionated using n-hexane.
Figure 26:
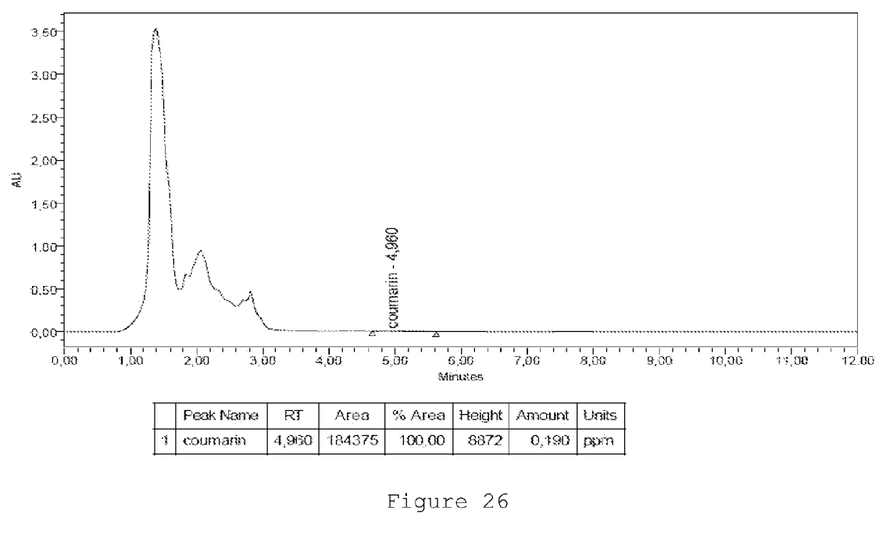
FIG. 26 is a high performance liquid chromatogram of substantially coumarin-free extract of *Cinnamomum burmanii* extracted using acetone and fractionated using n-hexane.

The result showed that peak of the standard coumarin compound could be seen in 5.099 retention time. The crude extract of *Cinnamomum burmanii* obtained from the extraction process using water, alcohols and acetone showed peaks which represent the coumarin compound. Specifically, as shown in FIG. 7, the crude extract obtained from water extraction showed peak at around 5.012 minutes. The crude extract obtained from alcohols extraction showed peak at around 5.012 minutes for ethanol and 5.007 minutes for methanol. The crude extract obtained from acetone extraction showed peak at around 5.011 minutes.

Contrary to that finding and accordance to the teaching of the present invention, the extract of *Cinnamomum burmanii* that have been fractionated using organic solvent(s) chloroform or n-butanol or ethyl acetate and/or n-hexane, did not show any peaks which represented coumarin. See FIG. 13-26. Therefore, the extract of *Cinnamomum burmanii* prepared according to the teaching of the present invention is substantially free of coumarin.

By comparing the peak area of coumarin standard of known concentration (50 ppm) with the peak area of crude extract and substantially coumarin-free extract shown at the same retention time with coumarin standard, the concentration of coumarin in that crude extract and substantially coumarin-free extract can be calculated.

TABLE 1

Coumarin content in *Cinnamomum burmanii* extract prepared through the teaching of this invention

| Extraction solvent(s) | Fractionation solvent | Coumarin content in crude extract (ppm) | Coumarin content in substantially coumarin-free extract (ppm) |
|---|---|---|---|
| Water | Chloroform | 3.04 | 0 |
|  | n-butanol |  | 0.16 |
|  | Ethyl acetate |  | 0.26 |
|  | n-hexane |  | 0.16 |
| Methanol and water | Chloroform | 19.28 | 0.08 |
|  | n-butanol |  | 0.09 |
|  | Ethyl acetate |  | 0.2 |
|  | n-hexane |  | 0.23 |
| Ethanol and water | Chloroform | 20.31 | 0.12 |
|  | n-butanol |  | 0.06 |
|  | Ethyl acetate |  | 0.39 |
|  | n-hexane |  | 0.17 |
| Acetone and water | Chloroform | 22.73 | 0.12 |
|  | n-butanol |  | 0.15 |
|  | Ethyl acetate |  | 0.16 |
|  | n-hexane |  | 0.19 |

EXAMPLE

Calculation of Average Tolerable *Cinnamomum burmanii* Extract Consumed

Tolerable Daily Intake of coumarin=0.1 mg/kg body weight
Average body weight=70 kg
Tolerable coumarin level consumed daily=7 mg coumarin
Coumarin level in crude extract ranging from 3.04-22.73 ppm or 3.04-22.73 mg coumarin/kg extract.
Tolerable extract consumed daily ranging from (7 mg coumarin)/(3.04 mg coumarin/kg extract) equal with 2.302 kg extract until (7 mg coumarin)/(22.73 mg coumarin/kg extract) equal with 0.31 kg extract.
The highest coumarin level in substantially coumarin-free extract=0.39 ppm=0.39 mg coumarin/kg extract.
The lowest tolerable extract consumed daily=7 mg coumarin/0.39 mg coumarin/kg extract=17.948 kg extract.

The data shown in Table. 1 suggests that the crude extract of *Cinnamomum burmanii* prepared through extraction process using water, alcohols and acetone (not more than 70% in water) contains high coumarin level. However, after the crude extract was fractionated by liquid-liquid extraction according to the teaching of the invention, the coumarin content becomes very low, even below the detection limit. Moreover, data shown in the example indicates that the substantially coumarin-free extract can be consumed in a wide range of quantity and does not pose any harm to the body, while consumable limit of the crude extract is very low. It shows that the value of the substantially coumarin-free extract is much below Tolerable Daily Intake (TDI) which is recommended by European Safety Authority (ESA). Therefore, the substantially coumarin-free extract of *Cinnamomum burmanii* prepared according to the teaching of this present invention is safe to be consumed daily and in long-term use.

Furthermore, this present invention also anticipates the use of substantially coumarin-free extract of *Cinnamomum burmanii* as a single active ingredient or in combination thereof as pharmaceutical composition or preparation to be safe for daily and long-term consumption.

F. Industrial Application

Extract or pharmaceutical dosage forms of the substantially coumarin-free extract of *Cinnamomum burmanii* can be used in industrial scale in the production of extract, powder extract, and/or pharmaceutical dosage forms mainly for oral dosage form such as solid, semi-solid, or liquid or food and beverage.

The invention claimed is:
1. A process for the preparation of substantially coumarin-free extract derived from *Cinnamomum burmanii*, comprising:
grinding raw material of *Cinnamomum burmanii* to obtain a ground material;
macerating said ground material in a first solvent for a time sufficient to produce a crude extract containing coumarin, wherein the first solvent is selected from a group consisting of water, alcohol, acetone or a combination thereof, to obtain a macerated material;
filtering said macerated material to obtain a filtrate;
concentrating said filtrate to obtain a crude extract;

fractionating said crude extract by liquid-liquid extraction with a second solvent selected from a group consisting of chloroform, n-butanol, ethyl acetate and n-hexane, to obtain a purified extract having a maximum coumarin level of 0.39 ppm;
   wherein said first solvent is immiscible in said second solvent; and
   wherein the weight ratio of said crude extract and said second solvent is about 1:1 to 1:2.

2. The process according to claim 1 further comprises drying said purified extract.

\* \* \* \* \*